United States Patent [19]

McGraw

[11] 4,437,937

[45] Mar. 20, 1984

[54] CONTINUOUS TRICKLE-DOWN DISTILLATION UNIT FOR PRODUCING HYDRATED ALCOHOL

[76] Inventor: Thomas F. McGraw, 9034 Ashmeade Dr., Fairfax, Va. 22032

[21] Appl. No.: 327,135

[22] Filed: Dec. 3, 1981

[51] Int. Cl.³ .......................... B01D 3/28; C07C 29/80
[52] U.S. Cl. .................... 202/160; 202/180; 202/181; 202/182; 202/185 B; 202/185 E; 202/206; 202/234; 202/236; 202/267 R; 203/1; 203/19; 203/86; 203/DIG. 13; 203/DIG. 22
[58] Field of Search ............. 202/158, 176, 181, 179, 202/180, 198, 182, 185 B, 161, 185 R, 185 E, 206, 267, 197; 203/86, 1, 25, DIG. 22, 19, DIG. 13; 426/493, 494; 261/97, DIG. 72

[56] References Cited

U.S. PATENT DOCUMENTS

| | | | |
|---|---|---|---|
| 435,005 | 5/1891 | Holden | 202/158 |
| 1,577,675 | 3/1926 | Ballman | 202/185 B |
| 1,822,454 | 9/1931 | Ricard et al. | |
| 1,830,469 | 11/1931 | Keyes | |
| 1,864,021 | 6/1932 | Jack | 202/206 |
| 3,156,629 | 11/1964 | Ester | 203/84 |
| 3,340,157 | 9/1967 | Weiss | 202/180 |
| 3,361,646 | 1/1968 | MacMullan et al. | 202/206 |
| 3,607,662 | 9/1971 | Glover | 202/161 |
| 3,635,799 | 1/1972 | Lowi | 202/185 B |
| 3,796,657 | 3/1974 | Pretorius et al. | 261/DIG. 72 |
| 4,217,178 | 8/1980 | Katzen et al. | 203/19 |
| 4,306,940 | 12/1981 | Zenty | 203/DIG. 13 |
| 4,308,106 | 12/1981 | Mannfeld | 203/DIG. 13 |
| 4,314,890 | 2/1982 | Beck | 203/DIG. 13 |
| 4,329,206 | 5/1982 | Cartland | 203/DIG. 13 |

Primary Examiner—Wilbur L. Bascomb, Jr.
Attorney, Agent, or Firm—Donald J. Singer; Jacob N. Erlich

[57] ABSTRACT

A continuous trickle-down distillation unit for producing hydrated alcohol having a compact, elongated distillation tube through which a fluid mixture including alcohol as one of its constituents passes. Within the distillation tube only the alcohol-predominant portion of the fluid mixture is vaporized while the remaining constituents of the fluid mixture are removed. The vaporized alcohol-predominant portion is condensed within a chamber which communicates with the distillation tube and is removed therefrom by a collection plate which extends partially into the chamber.

4 Claims, 3 Drawing Figures

CONTINUOUS TRICKLE-DOWN DISTILLATION UNIT FOR PRODUCING HYDRATED ALCOHOL

STATEMENT OF GOVERNMENT INTEREST

The invention described herein may be manufactured and used by or for the Government for governmental purposes without the payment of any royalty thereon.

BACKGROUND OF THE INVENTION

This invention relates generally to a system for producing alcohol, and, more particularly, to a small, compact continuous trickle-down distillation unit for producing hydrated alcohol.

As fossil fuels become more and more expensive to obtain it is becoming increasingly important to find alternative methods of producing fuel for various types of vehicles such as automobiles and trucks. In selecting these alternative fuel producing methods, it is necessary to consider only those procedures which minimize or completely eliminate dependence upon high-cost crude oil for fuel production.

It is becoming abundantly clear that the utilization of distillation procedures for recovering alcohol from fermentation or synthetic feedstocks may be a desirable alternative to the methods of producing fuels already in existence today. Unfortunately, as pointed out in U.S. Pat. No. 4,217,178 a major drawback within such methods is the high operating cost of conventional distillation systems. One cause of this high operating cost is the high thermal energy requirements of systems which produce anhydrous alcohol.

Furthermore, distillation techniques in use today involve the heating of the mixture to be distilled beyond the boiling point of all the mixture constituents, and then selectively cooling the vapor to separate them at a later period of time. Such a procedure not only requires a large heat source but also, because of the danger involved in its use, is not readily adaptable for a noncommercial application.

It has recently been shown that hydrated alcohol (low proof alcohol) can be efficiently burned in spark-ignited internal combustion engines with minor modifications of the engine. In fact, it has been shown that vehicles are now capable of operating on alcohol which is as impure as 160 proof.

It therefore would be highly desirable to provide a distillation unit which is capable of producing hydrated alcohol in a simple, safe and highly economical manner. In addition it would be extremely important if such a distillation unit could be manufactured as a small unit operable by private individuals.

SUMMARY OF THE INVENTION

The present invention overcomes the problems encountered in the past and as set forth in detail hereinabove by providing a distillation unit capable of economically producing hydrated alcohol. The unit is simple in construction, highly energy-efficient and extremely safe to use.

The continuous trickle-down distillation unit of this invention bases its operation upon a technique of trickling the mixture to be distilled through a heated labyrinth-like diffusion core in conjunction with a careful restriction of the distillation heat below that necessary to evaporate the water within the mixture. The mixture encounters sufficient heat in the diffusion core to evaporate and thus strip the alcohol-predominant portion from the water-predominant portion. The portion with the highest water concentration trickles down and is removed from the unit by a discharge pipe. The portion with the highest alcohol concentration is vaporized and cooled in a subsequent procedure and removed in liquid form from the distillation unit.

In the distillation unit of this invention there is no need for an expensive reservoir for containing the mixture while it is brought to a boil as with prior techniques. While selective heat is utilized in this invention to perform the actual distillation procedure, the distillate is condensed by a fairly unselective cooling technique.

It is therefore an object of this invention to provide a continuous trickle-down distillation unit capable of producing hydrated alcohol.

It is another object of this invention to provide a distillation unit which is extremely compact and simple to operate.

It is still another object of this invention to provide a distillation unit which is extremely safe in that no high temperatures or pressures are utilized within the system.

It is a further object of this invention to provide a distillation unit which is continuous in operation and can operate essentially unattended as long as it is fed a fluid mixture to be distilled.

It is still a further object of this invention to provide a distillation unit which is extremely energy-efficient, and does not require heat to excessive temperatures or complex and large reservoirs for containing the fluid mixture to be distilled.

It is still a further object of this invention to provide a distillation unit which requires no further distillation of the finished product.

It is still another object of this invention to provide a distillation unit which is economical to produce and which utilizes conventional, currently available, components that lend themselves to standard mass producing manufacturing techniques.

For a better understanding of the present invention, together with other and further objects thereof, reference is made to the following description taken in conjunction with the accompanying drawing and its scope will be pointed out in the appended claims.

DETAILED DESCRIPTION OF THE DRAWING

DETAILED DESCRIPTION OF THE PREFERRED EMBODIMENT

Figure 1:
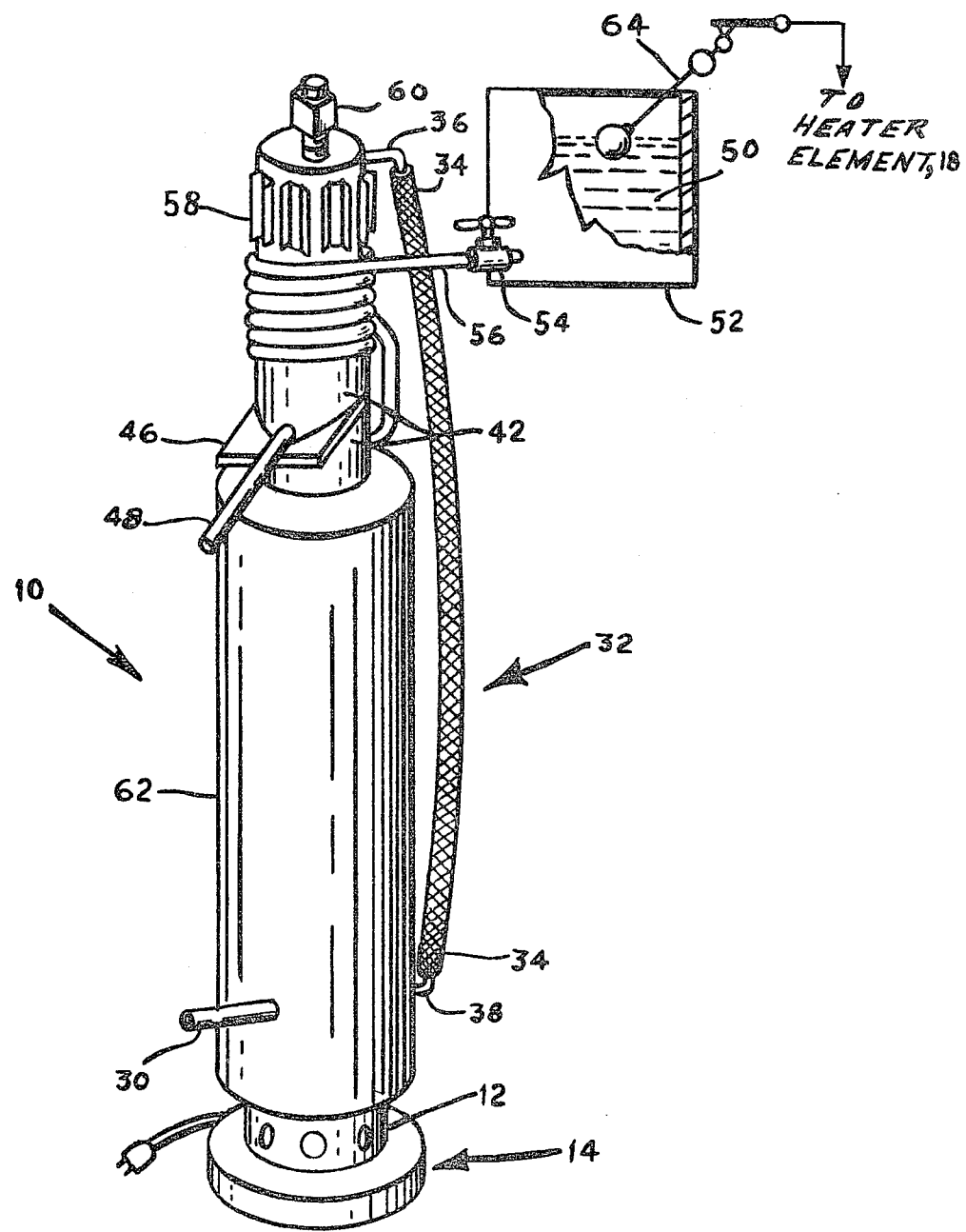
FIG. 1 is a pictorial representation of the continuous trickle-down distillation unit of this invention.
Figure 2:
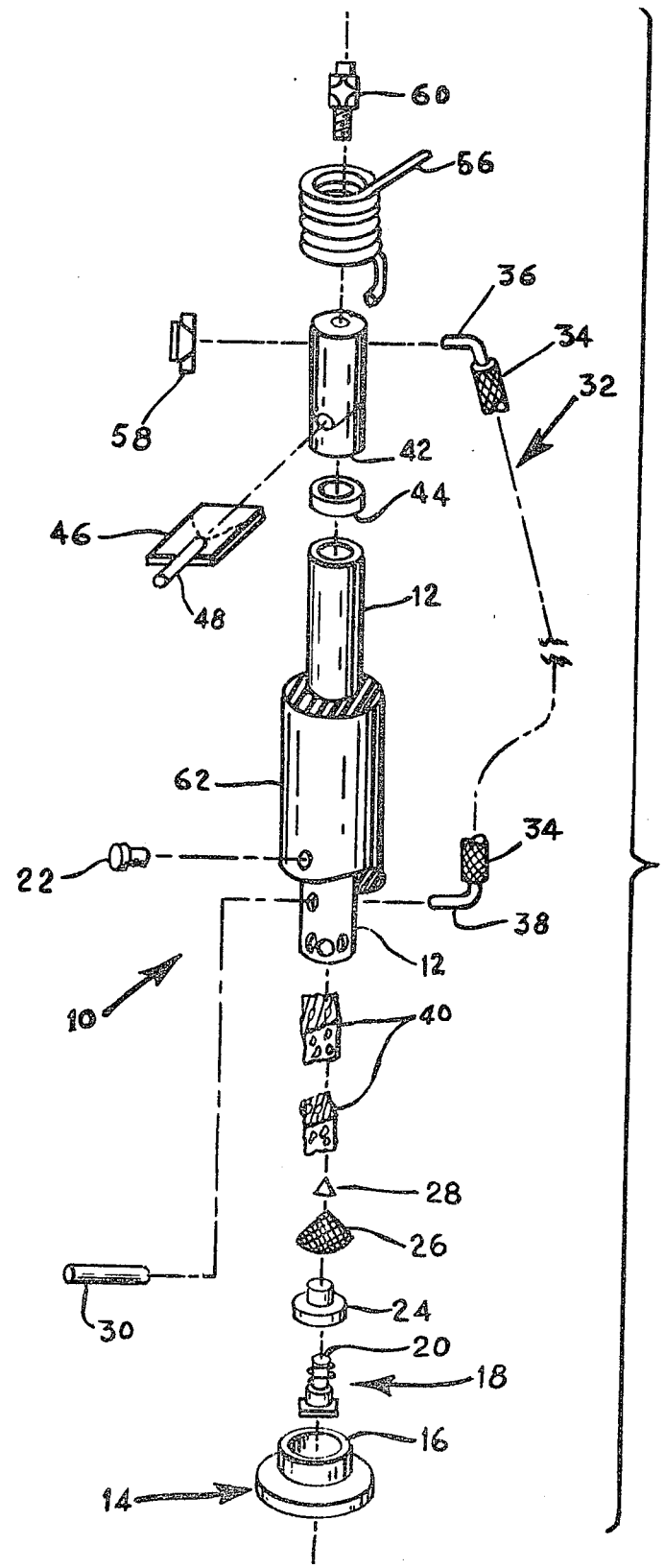
FIG. 2 is an exploded, pictorial representation of the components making up the continuous trickle-down distillation unit of this invention.

Reference is now made to FIGS. 1 and 2 of the drawing to clearly illustrate the components which make up the continuous trickle-down distillation unit 10 of this invention capable of producing hydrated alcohol. The main component of the distillation unit 10 of this invention is a compact, elongated, preferably cylindrically-shaped distillation tube 12. Tube 12 may be made of any suitable material such as copper or stainless steel and is preferably approximately 3 inches in diameter and not less than four feet in length. Although the specific dimensions of tube 12 may be varied within the scope of this invention, they have been given to illustrate that the overall size of distillation unit 10 is extremely small and compact. Furthermore, the longer the length of distillation tube 12 the greater the flow rate which may pass therethrough.

Tube 12 is supported upon a base 14 having an upstanding cylindrically shaped element 16 thereon which is formed so as to fit within and stabilize tube 12 in its upright position. A conventional thermostatically-controlled electric heater 18 is mounted in base 14. Heater 18 preferably utilizes a 600 watt or less heater element 20. Temperature control of heater 18 is maintained by a conventional thermostat 22 which is electrically connected to heater 18. Proper adjustment of thermostat 22 regulates the temperature of heater element 20 to a temperature in the range of approximately 170 to 180 degrees, the heat of vaporization of alcohol.

It is essential with this invention that the temperature produced by heater 18 be less than the heat of vaporization of the water content of the fluid mixture to be distilled. Therefore, thermostatic control of heater 18 is critical. By so doiing, the distillation unit 10 of this invention avoids the energy waste of traditional approaches. By proper temperature control it is possible to selectively evaporate the alcohol-predominant portion of the water/alcohol matrix of the distillation mixture in a manner described in detail hereinbelow.

Still referring to FIG. 2, circumscribing heater 18 is a water collection ring 24. Situated above heater 18 and ring 24 is a conically shaped metallic screen preferably made of copper, which directs the waste water from the distillation mixture flowing down tube 12 away from heating element 20. In addition, a deflector cone 28 is positioned above screen 26. Cone 28 is also preferrably made of sheet copper and prevents the direct wetting of heater 18. Therefore as water trickles down tube 12 it is directed into the water collection ring 24 which directs this waste water out of tube 12 by means of exit tube 30.

The central part of distillation tube 12 is filled with a diffusion core 40 in the form of, for example, a labyrinth-like glass or ceramic material which is utilized to maximize the surface area through which the distillation mixture passes while it contacts the heated air. The material which makes up this diffusion core 40 should be one which does not break down when exposed to heat or alcohol.

An expansion chamber 42 is secured to the top of distillation tube 12 by means of sleeve 44 and held in place by any suitable securing method such as soldering. Located within expansion chamber 42 is a hydrated alcohol collector plate 46. Hydrated alcohol collector plate 46 fits within expansion chamber 42 at an angle and only passes part way therethrough in order to allow the alcohol-predominant vapor to pass therearound before being condensed into hydrated alcohol and caught by collector plate 46. Attached to collector plate 46 is a hydrated alcohol outlet pipe 48 through which the recovered or condensed hydrated alcohol passes.

In addition, distillation unit 10 of this invention includes therein a vapor return system 32 made up of a tubular line 34 and suitable fittings 36 and 38 which connect line 34 to tube 12. Line 34 allows the vapor which does not condense during the distillation process to be redirected back through the system in a manner described below.

The distillation mixture 50, in the form of a fluid mixture more commonly referred to as "beer", is contained within a distillation storage vessel 52 shown in FIG. 1 of the drawing. Mixture 50 is formed from any suitable mash or the like. Although this invention does not focus upon the source of mash, any suitable raw material such as obtained from scraps, bruised or spoiled fruit, tainted food, and the like which can be broken down with a yeast to produce alcohol can be utilized with this invention. Furthermore, since this invention is designed for individual consumers, these sources which are fairly realistic in price are capable of providing mash essentially free.

The fluid mixture 50 or "beer" which is contained within vessel 52 passes through a conventional adjustable flow rate valve 54 into tube 12 as shown in FIG. 1 of the drawing. Flow rate valve 54 connects vessel 52 to an inlet line 56 which encompasses expansion chamber 42 and may be soldered thereto. By encompassing expansion chamber 42 inlet line 56 can be used to preheat distillation mixture 50 as well as carry off heat from the chamber 42, and thus help encourage condensation.

In addition cooling fins 58 may be added to the expansion chamber 42 in order to optimize the cooling thereof. Cooling of the distillation unit 10 of this invention is thus passive and dependent upon convection from the surfaces of fins 58 of expansion chamber 42. Fins 58 and chamber 42 are preferably painted flat black to encourage cooling radiation. A pressure safety valve 60 is situated upon the top of the unit and completes the structure.

For purposes of enhancing the economy of operation any suitable insulation jacket 62 may encompass distillation tube 12. A conventional float-operated switch 64 on vessel 52 can be provided and be electrically connected to heater 18 so as to shut off heater 18 in the event that vessel 52 is no longer filled with fluid mixture 50.

MODE OF OPERATION

During operation, vessel 52 is continually filled with a water/alcohol fluid mixture 50, commonly called "beer" which is obtained during the fermentation process from mash. The purpose of the accumulator vessel 52 is to smooth out variations in delivery rate through distillation tube 12 and to assure a near-constant flow of fluid through tube 12. The flow rate valve 54 is adjusted to regulate the rate at which the fluid leaves vessel 52 and enters distillation tube 12.

Figure 3:
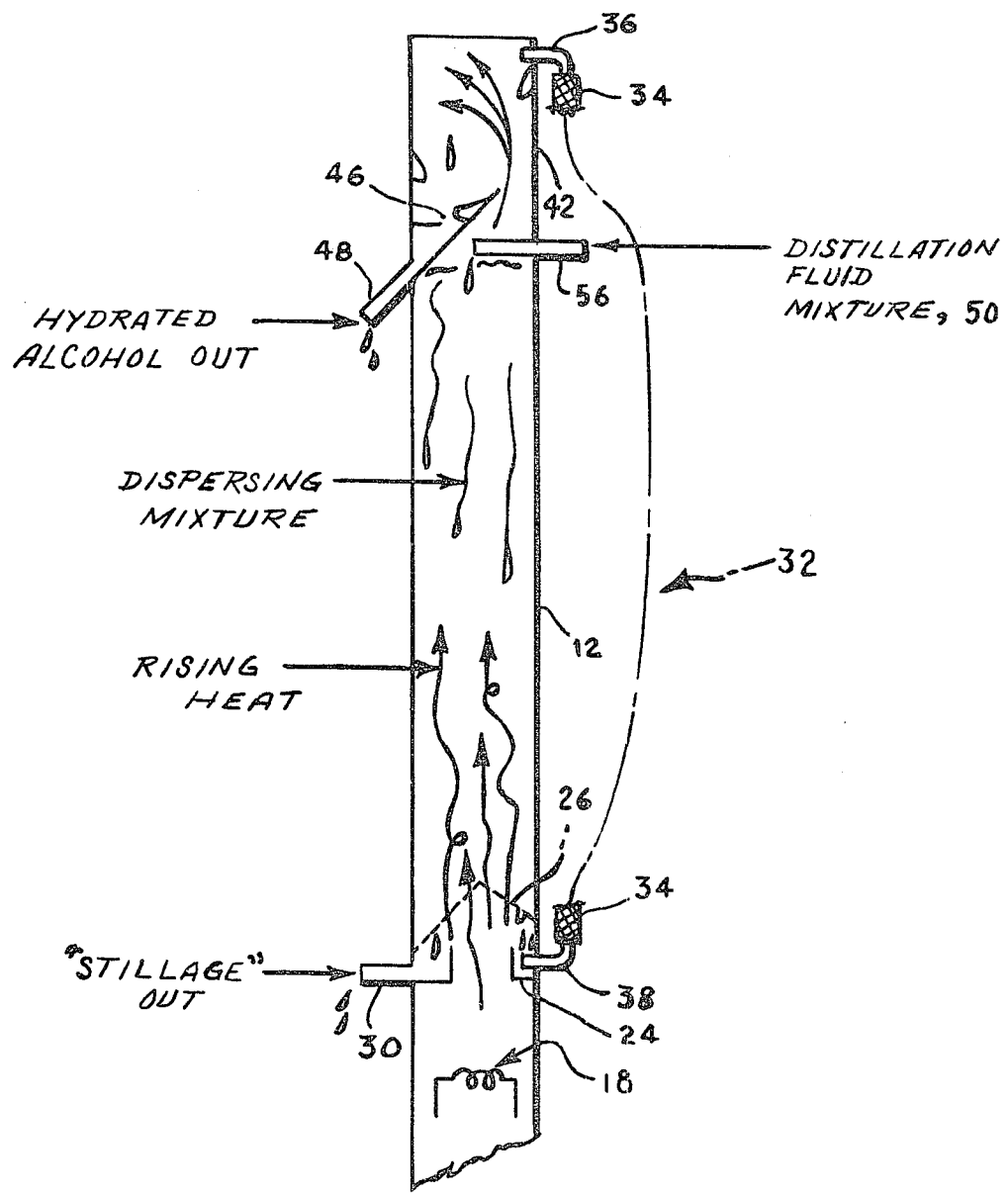
FIG. 3 is a schematic representation of the continuous trickle-down distillation unit of this invention illustrating the various steps during the production of hydrated alcohol.

As illustrated schematically in FIG. 3 of the drawing distillation fluid mixture 50 is brought into tube 12 by way of line 56 and passes through the labyrinth-like diffusion core 40 (shown in FIG. 2). As pointed out hereinabove this labyrinth-like structure or diffuser core 40 may be made of a crushed glass material preferably irregular, and made of fragments one square inch in size. Smaller pieces would not be utilized in order to avoid settling and thus plugging of the labyrinth. The fluid mixture 50 follows a tortuous path as gravity pulls the fluid mixture 50 to the bottom of tube 12.

It is preferable that the labyrinth-like surface area of diffuser core 40 be large so as to maximize the fluid contact with the heated air. The purpose of diffuser core 40 is to provide a means for lengthy exposure of the fluid mixture 50, in relatively thin flow, to air heated just beyond the vaporization temperature (170°–180° F.) of alcohol. The air temperature is also kept well below the temperature needed to vaporize the water in fluid mixture 50. Such an approach employed by this invention selectively evaporates the alcohol-predominant portion away from the water/alcohol matrix of fluid mixture 50.

The heat provided by heater 18 vaporizes the alcohol in a thin film heating process, that is, one in which the surface over which the fluid passes is maximized. Alcohol-predominant vapors, released by this thin-film heating process, rise in tube 12 until they pass the hydrated alcohol collector plate 46. After passing collector plate 46, the expansion chamber 42, which is passively cooled, condenses the alcohol-predominant vapor. Collector plate 46 is sloped to carry the distillate through the exit tube 48. Vapors reaching expansion chamber 42 but which do not condense there, are free to be convectively recirculated to the bottom of the labyrinth via the vapor return system 32.

A standard pressure release valve 60 prevents buildup of the dangerous pressures. Water and other waste liquids (stillage) which avoid vaporization, continue to flow to the bottom of tube 12 where they are deflected by walls of the tube 12 and carried off through tube 30 for disposal. The cone-shaped elements 26 and 28 prevent the water from reaching heater 18 while water collection ring 24 directs this waste fluid from tube 30. It is even possible to utilize this waste fluid as a crude antifreeze, since some alcohol will no doubt remain dissolved in it.

By the utilization of this invention it is possible to selectively evaporate alcohol from the water/alcohol mixture 50 so as to produce in an energy efficient manner hydrated alcohol in the 170-190 proof range.

Although this invention has been described with reference to a particular embodiment, it will be understood that this invention is also capable of further and other embodiments within the spirit and scope of the appended claims.

I claim:

1. A continuous trickle-down distillation unit for producing hydrated alcohol comprising:

means for containing a fluid mixture, said fluid mixture including alcohol and water;

a single, compact, elongated housing operably connected to and below said fluid mixture containing means for receiving said fluid mixture therefrom;

means situated within said elongated housing for increasing the surface area with which said fluid mixture comes in contact with as it passes therethrough, said surface area increasing means being in the form of a labyrinth-like structure made up of small fragments of material incapable of reacting with the constituents of said fluid mixture;

an electrical heater element operably connected within the bottom of said elongated housing for heating the interior of said housing and said labyrinth-like structure to a predetermined temperature, and means operably connected to said heater element for controlling said electrical heater element so as to maintain said predetermined temperature, said predetermined temperature being in the range of 170°–180° F., whereby alcohol-predominant vapors rise in said housing;

means in direct communication with said elongated housing for condensing said alcohol-predominant vapors into hydrated alcohol, said condensing means including a chamber and a plurality of fin-like elements protruding from said chamber for passively cooling said chamber;

means operably connected to said chamber for directing said hydrated alcohol out of said distillation unit, said directing means including a plate extending partially within said chamber for receiving said hydrated alcohol and directing said hydrated alcohol through an output line; and means operably connected to said elongated housing for directing remaining liquid constituents of said fluid mixture out of said distillation unit, said remaining liquid constituent directing means including means situated within said housing in the form of a cone-shaped element adjacent said heater element for preventing said remaining liquid constituents of said fluid mixture from contacting said heater element during the distillation process.

2. A continuous trickle-down distillation unit for producing hydrated alcohol as defined in claim 1 wherein said means for receiving said fluid mixture comprises a tube which interconnects said fluid mixture container with said housing, said tube also encompassing said chamber.

3. A continuous trickle-down distillation unit for producing hydrated alcohol as defined in claim 2 further comprising means interconnected between said chamber and said housing for passing uncondensed alcohol-predominant vapor from said chamber into said housing.

4. A continuous trickle-down distillation unit for producing hydrated alcohol as defined in claim 3 wherein said means for receiving said fluid mixture further comprises means for regulating the flow of said mixture into said housing, and said fluid mixture container includes therein means operably connected to said heater element for sensing the level of said fluid mixture within said container and for shutting off said heate element when the level of said fluid mixture drops below a preselected level within said container.

* * * * *